US008389699B2

(12) United States Patent
Rosenblum et al.

(10) Patent No.: US 8,389,699 B2
(45) Date of Patent: Mar. 5, 2013

(54) NUCLEIC ACID TERMINATORS INCORPORATING A CATIONIC MOIETY AND METHODS FOR THEIR USE

(75) Inventors: Barnett Rosenblum, San Jose, CA (US); Steven Menchen, Fremont, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 175 days.

(21) Appl. No.: 12/580,207

(22) Filed: Oct. 15, 2009

(65) Prior Publication Data

US 2010/0035326 A1 Feb. 11, 2010

Related U.S. Application Data

(62) Division of application No. 12/059,699, filed on Mar. 31, 2008, now abandoned.

(51) Int. Cl.
*C07H 21/00* (2006.01)
(52) U.S. Cl. ........................ 536/22.1; 435/975
(58) Field of Classification Search ................. None
See application file for complete search history.

(56) References Cited

U.S. PATENT DOCUMENTS

| | | | |
|---|---|---|---|
| 5,470,705 A | | 11/1995 | Grossman et al. |
| 5,489,523 A | * | 2/1996 | Mathur .................. 435/194 |
| 5,800,996 A | | 9/1998 | Lee et al. |
| 5,948,614 A | | 9/1999 | Chatterjee |
| 6,143,504 A | * | 11/2000 | Das et al. .............. 435/6.12 |
| 6,268,129 B1 | * | 7/2001 | Gut et al. .............. 435/5 |
| 6,811,979 B2 | | 11/2004 | Taing et al. |
| 6,818,760 B1 | | 11/2004 | Spicer et al. |
| 6,949,635 B1 | * | 9/2005 | Kumar et al. .......... 536/23.1 |

FOREIGN PATENT DOCUMENTS

| | | | |
|---|---|---|---|
| WO | 0119841 A1 | | 3/2001 |
| WO | WO 0119841 A1 | * | 3/2001 |
| WO | 2007/062243 A3 | | 5/2007 |
| WO | 2009/131805 A1 | | 10/2009 |

OTHER PUBLICATIONS

Finn et al., (Nucleic Acids Res. Aug. 15, 2003;31(16):4769-78).
Tabor, et al., "A single residue in DNA polymerases of the *Escherichia coli* DNA polymerase I family is critical for distinguishing between deoxy and dideoxyribonucleotides," Proc. Natl. Acad. Sci. USA, vol. 92, pp. 6339-6343, Jul. 1995.
Rosenblum, et al., "New dye-labeled terminators for improved DNA sequencing patterns," Nucleic Acids Research, vol. 25, No. 22, pp. 4500-4504, 1997.
PCT/US09/39015, "International Preliminary Report on Patentability mailed on Oct. 14, 2010", 12 pages.
PCT/US09/39015, "Partial Search Report Mailed Jul. 8, 2009", 6 pages.
PCTUS2009039015, "PCT/US2009/039015 International Search Report mailed Aug. 28, 2009", 23 pages.
Stavridis, M. P. et al., "A Discrete Period of FGF-Induced Erk1/2 Signalling is Required for Vertebrate Neural Specification", *Developement* (Cambridge, England), vol. 134, No. 16, XP002530550, ISSN: 0950-1991, The Whole Document, Aug 2007, pp. 2889-2894.
Storm, M. P. et al., "Regulation of Nanog Expression by Phosphoinositide 3-Kinase-Dependent Signaling in Murine Embryonic Stem Cells", *The Journal of Biological Chemistry*, vol. 282, No. 9, ISSN: 0021-6273, the whole Document ,XP002530549, Mar. 2, 2007, pp. 6265-6273.
Takahashi, K. et al., "Introduction of Pluripotent Stem Cells from Adult Human Fibroblasts by Defined Characters", vol. 131, No. 5, XP002478584, ISSN: 0092-8674 the whole document, Nov. 30, 2007, pp. 861-872.
Takahashi, K. et al., "Introduction of Pluripotent Stem Cells from Mouse Embryonic and Adult Fibroblast Cultures by Defined Characters", vol. 126, No. 4, XP003013968, ISSN: 0092-8674 , the whole Document, Aug. 25, 2006, pp. 663-676.

* cited by examiner

*Primary Examiner* — Christopher M. Babic

(57) ABSTRACT

Disclosed are methods and kits applicable to sequencing methods, such as Sanger dideoxy sequencing methods. The methods and kits disclosed utilize a cationically charged nucleic acid terminator in combination with a discriminatory polymerase.

13 Claims, 11 Drawing Sheets

FIG. 1

(A) (Cationic Moiety)$_n$—Z—X—S—B—L (B) Z—(Cationic Moiety)$_n$—X—S—B—L (C) Z—X—(Cationic Moiety)$_n$—S—B—L (D) Z—X—S—(Cationic Moiety)$_n$—B—L (E) Z—X—S—B—(Cationic Moiety)$_n$—L (F) Z—X—S—B—L—(Cationic Moiety)$_n$ (G) Z—X—S—B—L—(Cationic Moiety)$_n$—Reporter (H) Z—X—S—B—L—Reporter—(Cationic Moiety)$_n$ (I) Z—(Cationic Moiety)$_n$—X—S—B—L—(Cationic Moiety)$_n$ (J) Z—(Cationic Moiety)$_n$—X—S—B—L—Reporter n = 1 to 1000

SCHEME 1

SCHEME 2

SCHEME 3

SCHEME 4

SCHEME 5

SCHEME 6

SCHEME 7

NUCLEIC ACID TERMINATORS INCORPORATING A CATIONIC MOIETY AND METHODS FOR THEIR USE

CROSS-REFERENCE TO RELATED APPLICATIONS

This application is a divisional of application Ser. No. 12/059,699, filed Mar. 31, 2008, now abandoned, which is incorporated herein by reference.

FIELD

The present teachings relate generally to methods and kits that can be useful for sequencing.

BACKGROUND

The analysis of complex mixtures of polynucleotides is important in many biological applications. In many situations, it is necessary to separate components of such mixtures to detect target polynucleotides of interest, to determine the relative amounts of different components, and to obtain nucleotide sequence information.

Electrophoresis provides convenient methods for analyzing polynucleotides. Typically, polynucleotides can be separated on the basis of length, due to differences in electrophoretic mobility. For example, in a matrix such as a crosslinked polyacrylamide, polynucleotides typically migrate at rates that are inversely proportional to polynucleotide length, due to size-dependent obstruction by the crosslinked matrix. In free solution, polynucleotides tend to migrate at substantially the same rates because of their substantially identical mass to charge ratios, so that it is difficult to distinguish different polynucleotides based on size alone. However, distinguishable electrophoretic mobilities can be obtained in free solution using polynucleotides that contain different charge/mass ratios, e.g., by attaching to the polynucleotides a polymer or other chemical entity having a charge/mass ratio that differs from that of the polynucleotides alone (See, e.g., U.S. Pat. No. 5,470,705).

When different polynucleotides can be separated based on length or molecular weight, detection can usually be accomplished using a single detectable label, such as a radioisotope, fluorophore, or other suitable conventional label. However, in complex mixtures or when different-sequence polynucleotides have similar or identical mobilities, it is preferable to use two or more detectable labels to distinguish different polynucleotides unambiguously.

In DNA sequencing, it is now conventional to use two or more (usually four) different fluorescent (or other suitable) labels to distinguish sequencing fragments that terminate with one of the four standard nucleotide bases (A, C, G and T, or analogs thereof). Such labels are usually introduced into the sequencing fragments using suitably labeled extension primers or by performing primer extension in the presence of nonextendable nucleotides that contain unique labels. Electrophoresis of the labeled products generates ladders of fragments that can be detected on the basis of elution time or band position.

Currently, in Sanger dideoxy sequencing using labeled terminators, an exonuclease minus DNA polymerase that has a mutation that decreases the discrimination against dideoxynucleotides is utilized. Such a mutation is utilized because non-mutated polymerases typically incorporate deoxynucleotides at a rate that is several hundred to several thousand times that of dideoxynucleotides, resulting in unacceptably low dideoxynucleotide incorporation or unacceptably high artifacts and background during detection. Examples of mutated polymerases conventionally utilized in Sanger dideoxy sequencing include, for example, Taq DNA polymerase (F667Y) and E. coli DNA polymerase (F762Y).

The problem of preferential incorporation of deoxynucleotides over dideoxynucleotides utilizing non-mutated polymerases in Sanger dideoxy sequencing, as well as other problems discussed herein, are obviated by the present teachings.

SUMMARY

The present teachings, among other methods and kits, provide a method of sequencing a target polynucleotide. The method comprises providing a cationically charged nucleic acid terminator wherein the cationically charged nucleic acid terminator comprises a labeled compound of the form Z—X—S—B-L, wherein Z is a mono-, di, or triphosphate or thiophosphate, or corresponding boranophosphate, X is O, $CH_2$, S, or NH, S is a sugar or sugar analogue, B is a naturally occurring or a synthetic base or nucleobase, L is linker that is alkyl, alkenyl, or alkynyl, wherein at least one of L, B, S, X or Z is substituted with a moiety which imparts a positive charge to the labeled compound, wherein at least one of L, B, S, X or Z is substituted with a reporter moiety, reacting the cationically charged nucleic acid terminator with a discriminatory polymerase that is exonuclease minus, separating the reacted cationically charged nucleic acid terminator on the basis of size, and determining the sequence of the target polynucleotide sequence.

The present teachings also provide a kit for sequencing polynucleotides. The kit comprises a cationically charged nucleic acid terminator that comprises a labeled compound of the form Z—X—S—B-L, wherein Z is a mono-, di, or triphosphate or thiophosphate, or corresponding boranophosphate, X is O, $CH_2$, S, or NH, S is a sugar or sugar analogue, B is a naturally occurring or a synthetic base or nucleobase, L is a linker that is alkyl, alkenyl, or alkynyl, and wherein at least one of L, B, S, X or Z is substituted with a moiety which imparts a positive charge to the labeled compound, and wherein at least one of L, B, S, X, or Z is substituted with a reporter moiety, and a discriminatory polymerase that is exonuclease minus.

In some embodiments of the present teachings, the cationic moiety that imparts a positive charge can be an amine, a higher alkyl amine, an aryl amine or an imidazole.

In some embodiments of the present teachings, the cationically charged nucleic acid terminator can include 1, 2, 3, 4, 5, 6, 7, 8, 9, 10, or even more cationic moieties to impart the cationic charge to the nucleic acid terminator.

In some embodiments of the present teachings, the discriminatory polymerase can be an *Escherichia coli* DNA polymerase.

In some embodiments of the present teachings, the discriminatory polymerase can be a *Thermus aquaticus* DNA polymerase.

In some embodiments of the present teachings, the discriminatory polymerase can be a Pfu DNA polymerase from *Pyrococcus furiosus*.

In some embodiments of the present teachings, the discriminatory polymerase can be a DNA polymerase from *Bacillus stearothermophilus*.

In some embodiments of the present teachings, L is substituted with a reporter moiety.

These and other features of the present teachings are set forth herein.

DRAWINGS

The skilled artisan will understand that the drawings, described below, are for illustration purposes only. The drawings are not intended to limit the scope of the present teachings in any way.

Embodiments of the present teachings will now be described with reference to the drawings in which:

FIGS. 1(A)-1(J) show examples of positioning of a cationic moiety or cationic moieties on the cationically charged nucleic acid terminator.

DESCRIPTION OF VARIOUS EMBODIMENTS

Figure 2:
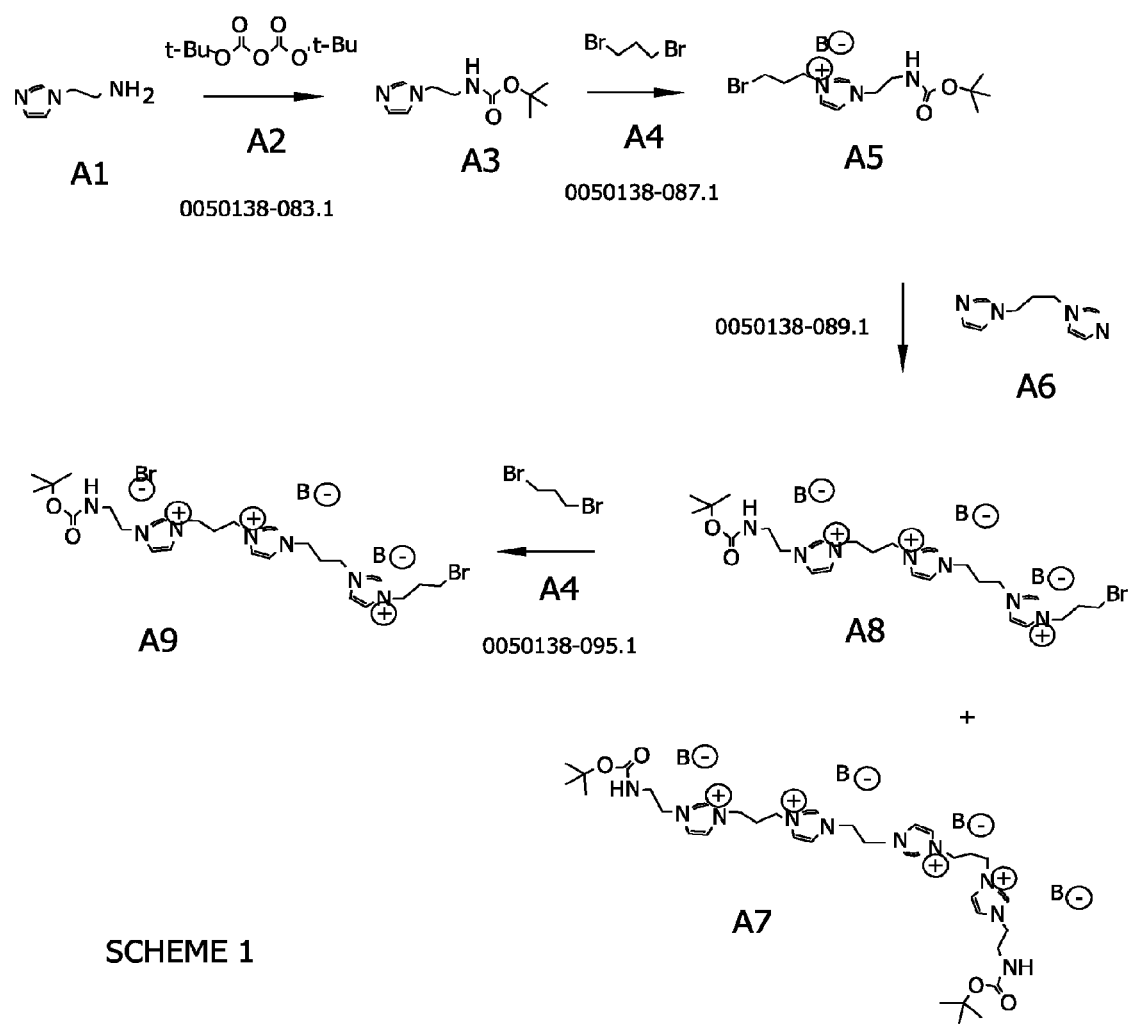
FIGS. 2-9 show various chemical schemes referred to in the Examples for synthesizing a cationically charged nucleic acid terminator.
Figure 3:
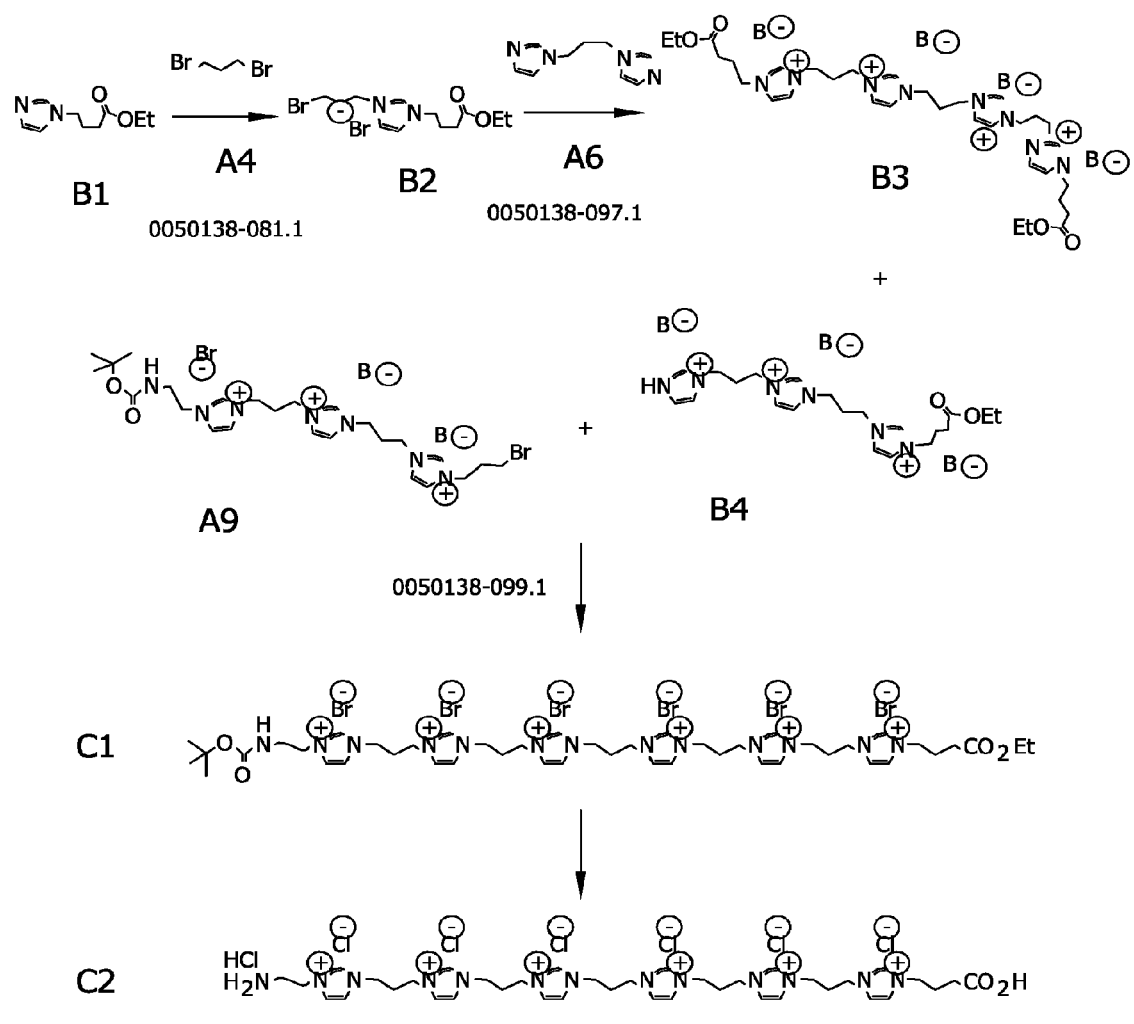
Figure 4:
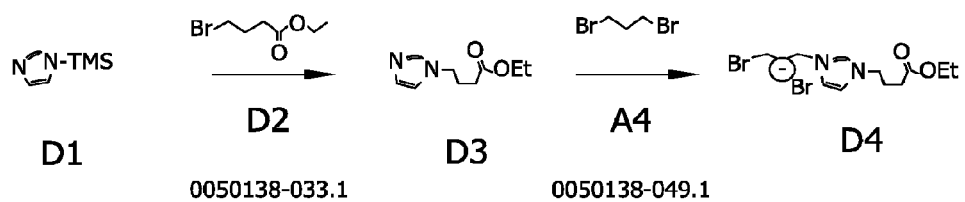
Figure 4:
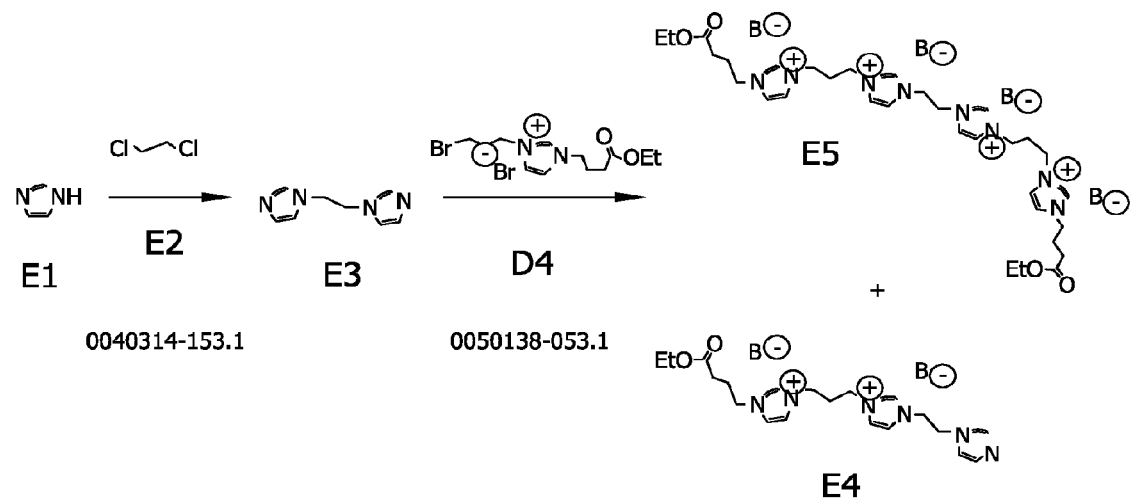
Figure 5:
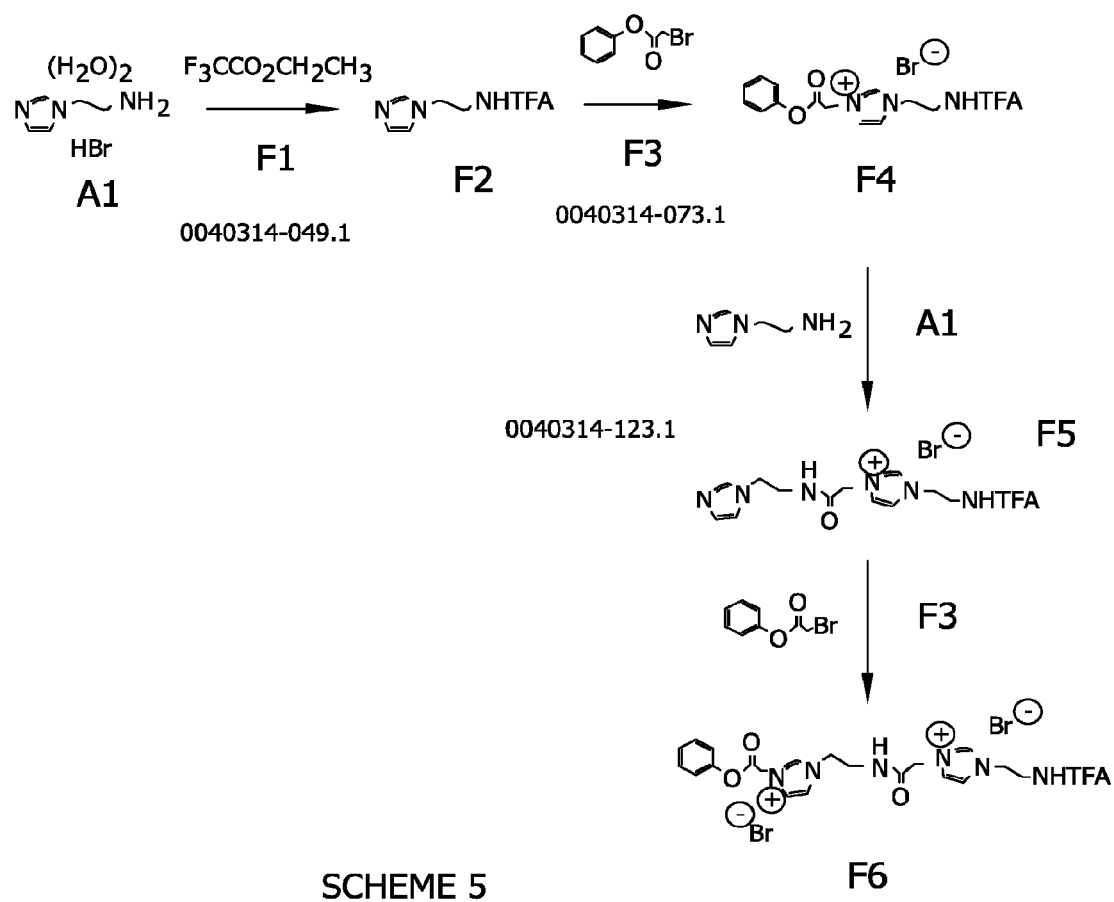
Figure 6:
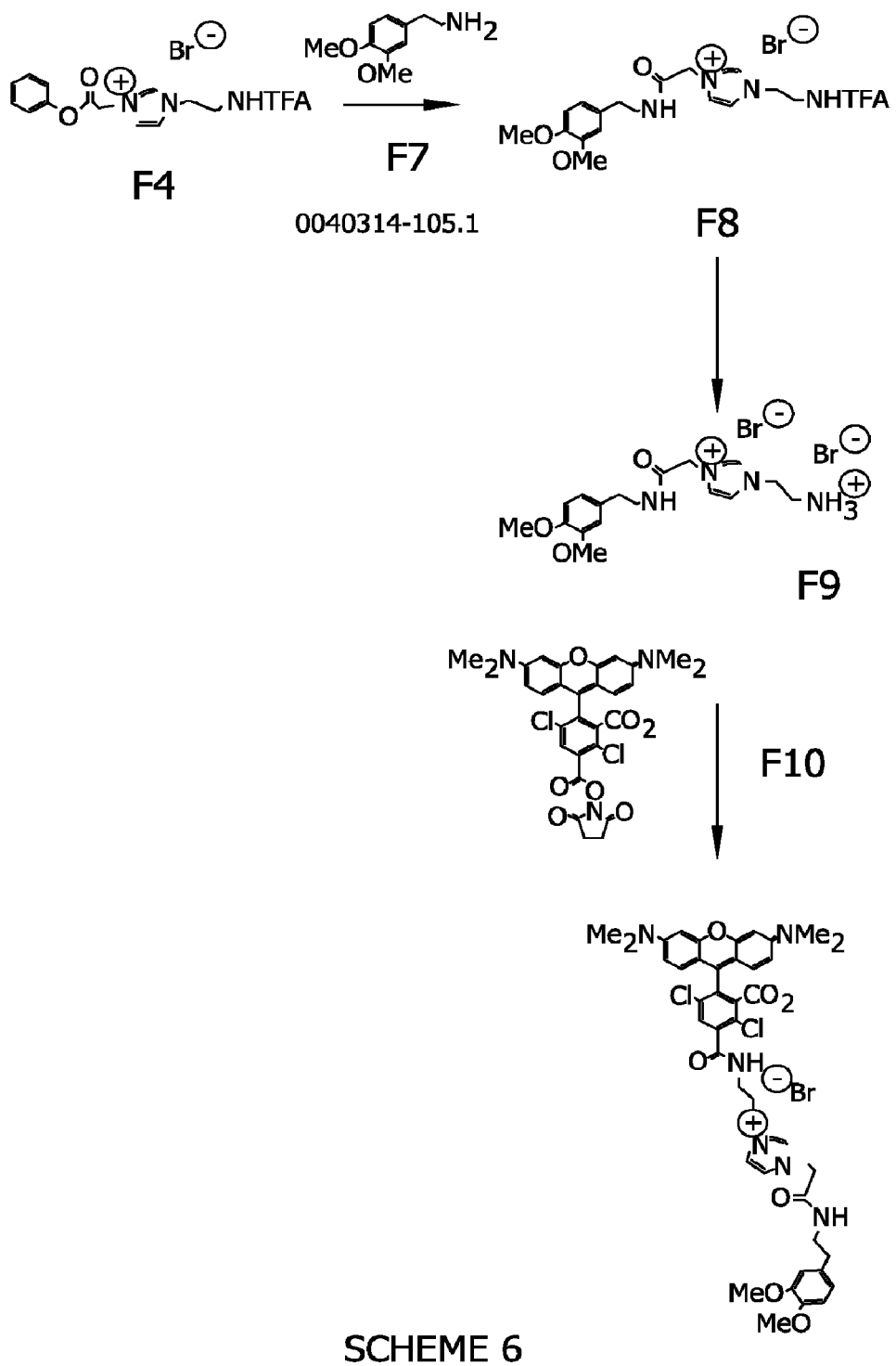
Figure 7:
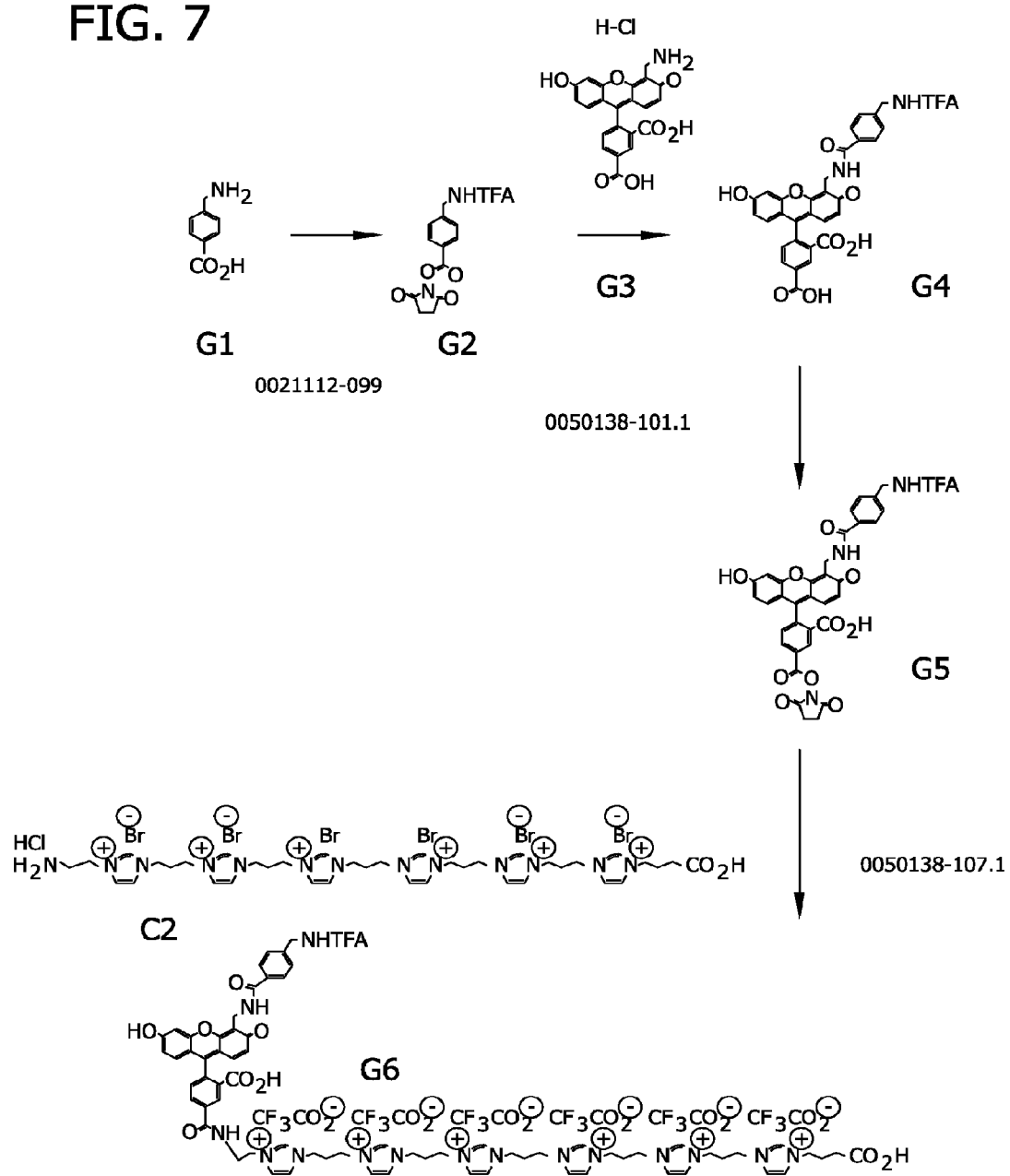
Figure 8:
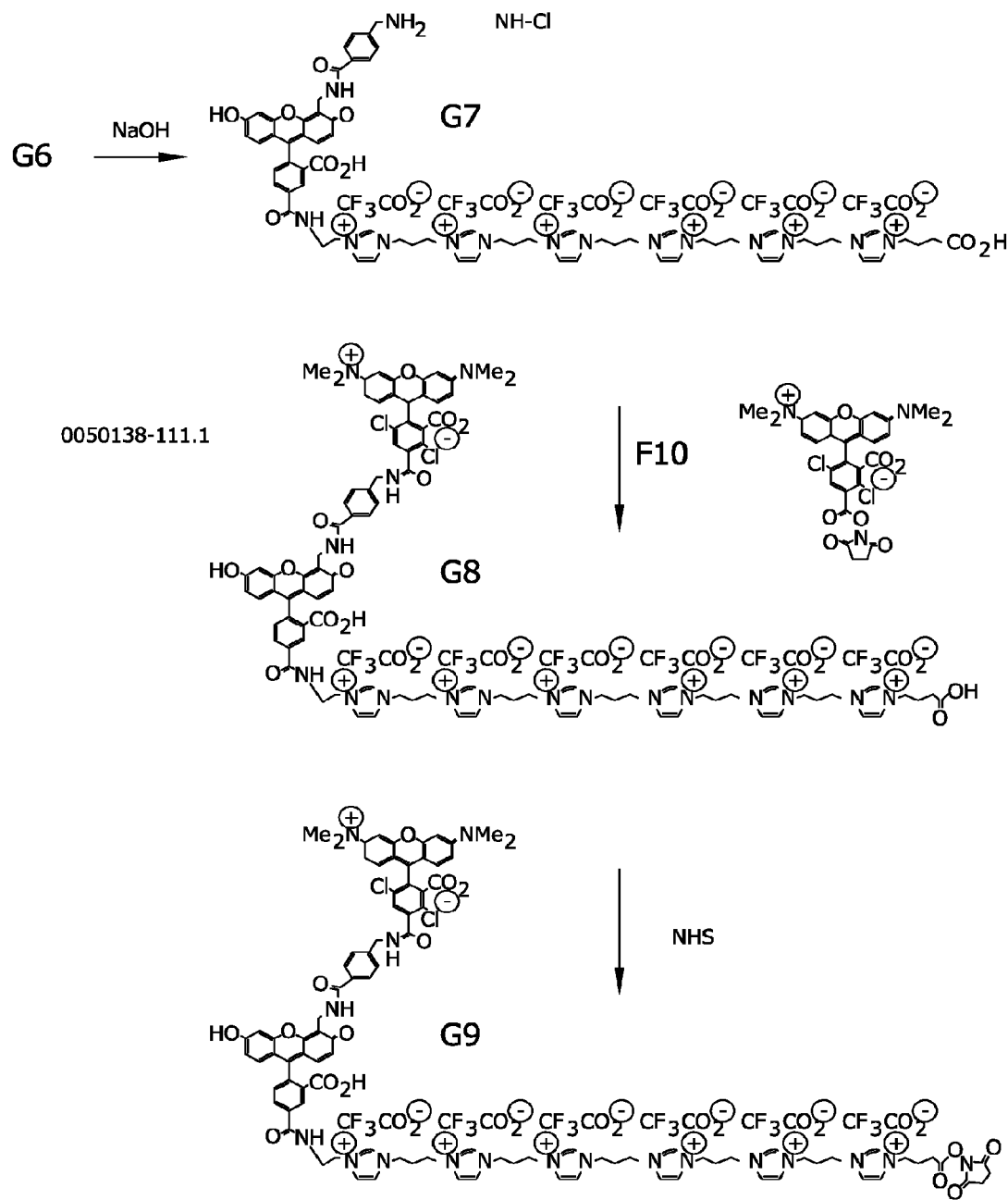
Figure 9:
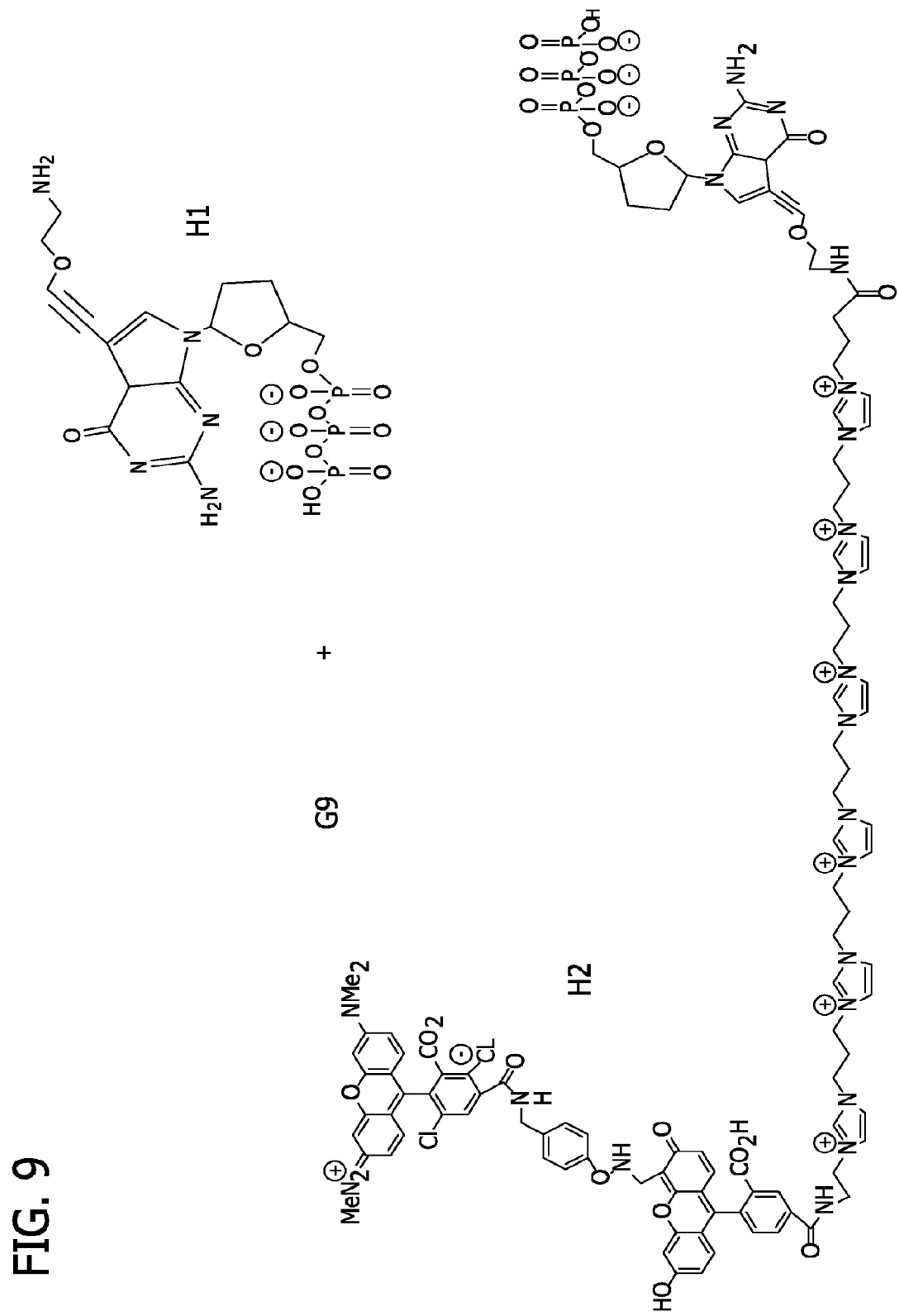

Before describing the present teachings in detail, it is to be understood that these teachings are not limited to specific compositions, kits, process steps, or equipment, as such can vary. It should also be understood that the terminology used herein is for the purpose of describing various embodiments only, and is not intended to be limiting. Methods recited herein can be carried out in any order of the recited events that is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described can be set forth and claimed independently, or in combination with any one or more of the features described herein.

Unless defined otherwise below, all technical and scientific terms used herein have the same meaning as commonly understood by one of ordinary skill in the art to which this disclosure belongs. Certain elements are defined herein for the sake of clarity.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting.

In describing and claiming the present invention, the following terminology will be used in accordance with the definitions set out below.

A "discriminatory polymerase" refers to a polymerase that incorporates deoxynucleotides at a rate that is at least two times greater than the incorporation of dideoxynucleotides in a conventional Sanger dideoxy sequencing method. Examples of a "discriminatory polymerase" include *Thermas aquaticus* DNA polymerase, *Escherichia coli* DNA polymerase I, Pfu DNA polymerase from *Pyrococcus furiosus*, and DNA polymerase from *Bacillus stearothermophilus*. Polymerases that have a mutation to specifically reduce their discrimination of dideoxynucleotides as compared to deoxynucleotides in a conventional Sanger dideoxy sequencing method are not considered to be a "discriminatory polymerase." Example polymerases that contain a mutation to reduce the discrimination of dideoxynucleotides include Taq DNA polymerase (Taq F667Y) and *E. coli* DNA polymerase (*E. coli* F762Y). (See Tabor, S. & Richardson, C. C., *Proc. Natl. Acad. Sci.* USA Vol. 92, pp. 6339-6343, July 1995).

"Exonuclease" refers to a nuclease that releases one nucleotide at a time (serially) beginning at one end of a polynucleotide.

An "exonuclease minus" polymerase refers to a polymerase that has had substantially all exonuclease activity removed therefrom.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc., and the like.

"Alkenyl" refers to an unsaturated branched, straight-chain or cyclic alkyl radical having at least one carbon=carbon double bond derived by the removal of one hydrogen atom from a single carbon atom of a parent alkene. The radical can be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like.

"Alkynyl" refers to an unsaturated branched, straight-chain or cyclic alkyl radical having at least one carbon≡carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc., and the like.

"Polynucleotide" and "oligonucleotide", which are used interchangeably herein, refer to linear polymers of natural nucleotide monomers or analogs thereof, including for example, double- and single-stranded deoxyribonucleotides, ribonucleotides, a-anomeric forms thereof, and the like. A polynucleotide can be composed entirely of deoxyribonucleotides, ribonucleotides, or analogs thereof, or can contain blocks or mixtures of two or more different monomer types. Usually nucleoside monomers are linked by phosphodiester linkages. However, polynucleotides and oligonucleotides containing non-phosphodiester linkages are also contemplated. "Polynucleotide" and "oligonucleotide" also encompass polymers that contain one or more non-naturally occurring monomers and/or intersubunit linkages, such as peptide nucleic acids (PNAs, e.g., polymers comprising a backbone of amide-linked N-(2-aminoethyl)-glycine subunits to which nucleobases are attached via the non-amide backbone nitrogens. See Nielsen et al., Science 254:1497-1500 (1991)). Polynucleotides typically range in size from a few monomeric units, e.g. 8-40, to several thousand monomeric units.

"Nucleobase" refers to a nitrogen-containing heterocyclic moiety capable of forming Watson-Crick type hydrogen bonds with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of naturally occurring nucleobases, e.g. 7-deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, $O^6$-methylguanine, $N^6$-methyl-adenine, $O^4$-methylthymine, 5,6-dihydrothymine, 5,6-dihydrouracil, 4-methylindole, and ethenoadenine (Fasman, Practical Handbook of Biochemistry and Molecular Biology, pp. 385-394, CRC Press, Boca Raton, Fla. (1989)).

"Nucleotide" refers to a phosphate ester of a nucleoside, either as an independent monomer or as a subunit within a polynucleotide. Nucleotide triphosphates are sometimes denoted as "NTP", "dNTP" (2'-deoxypentose) or "ddNTP" (2',3'-dideoxypentose) to particularly point out the structural features of the ribose sugar. "Nucleotide 5'-triphosphate" refers to a nucleotide with a triphosphate ester group at the 5' position. The triphosphate ester group can include sulfur substitutions for one or more phosphate oxygen atoms, e.g. -thionucleotide 5'-triphosphates.

"Terminator" refers to an enzymatically incorporatable nucleotide which prevents subsequent incorporation of nucleotides to the resulting polynucleotide chain and thereby halts polymerase-mediated extension. Typical terminators lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose, for example. Alternatively, a ribofuranose analog can be used, such as 2',3'-dideoxy-b-D-ribofuranosyl, b-D-arabinofuranosyl, 3'-deoxy-b-D-arabinofuranosyl, 3'-amino-2',3'-dideoxy-b-D-ribofuranosyl, and 2',3'-dideoxy-3'-fluoro-b-D-ribofuranosyl (see, for example, Chidgeavadze et al., Nucleic Acids Res., 12: 1671-1686 (1984), and Chidgeavadze et al. FEB. Lett., 183: 275-278 (1985)). Nucleotide terminators also include reversible nucleotide terminators such as $N^6$-(2-nitrobenzyl)-2'-deoxyadenosine triphosphates (Metzker et al. Nucleic Acids Res., 22(20):4259 (1994)) and Wu et al. Nucleic Acids Res., 35(19):6339 (2007).

"Nucleoside" refers to a compound comprising a nucleobase linked to a C-1' carbon of a ribose sugar or sugar analog thereof. The ribose or analog can be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently —H, $C_1$-$C_6$ alkyl or $C_3$-$C_{14}$ aryl. Particularly preferred riboses are ribose, 2'-deoxyribose, 2',3'-dideoxyribose, 3'-haloribose (such as 3'-fluororibose or 3'-chlororibose) and 3'-alkylribose. Typically, when the nucleobase is A or G, the ribose sugar is attached to the $N^9$-position of the nucleobase. When the nucleobase is C, T or U, the pentose sugar is attached to the $N^1$-position of the nucleobase (Kornberg and Baker, DNA Replication, $2^{nd}$ Ed., Freeman, San Francisco, Calif., (1992)). Other examples of sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NR or halogen groups, where each R is independently —H, $(C_1$-$C_6)$ alkyl or $(C_1$-$C_{14})$ aryl. Examples of substituted furanoses having 5 ring atoms include but are not limited to 2'-deoxyribose, 2'-$(C_1$-$C_6)$alkylribose, 2'-$(C_1$-$C_6)$alkoxyribose (e.g., 2'-O-methyl ribose), 2'-$(C_5$-$C_{14})$ aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-amino-ribose, 2'-deoxy-3'-$(C_1$-$C_6)$alkylribose, 2'-deoxy-3'-$(C_1$-$C_6)$alkoxyribose, 2'-deoxy-3'-$(C_5$-$C_{14})$aryloxyribose, 3'-$(C_1$-$C_6)$ alkylribose-5'-triphosphate, 2'-deoxy-3'-$(C_1$-$C_6)$ alkylribose-5'-triphosphate, 2'-deoxy-3'-$(C_1$-$C_6)$ alkoxyribose-5'-triphosphate, 2'-deoxy-3'-$(C_5$-$C_{14})$ aryl-oxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs include but are not limited to, locked nucleic acids such as

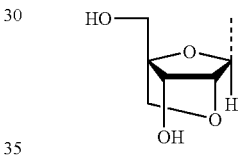

(e.g., see Wengel, et al. WO 99/14226, incorporated herein by reference).

Generally, whenever the cationically charged nucleic acid terminator is mentioned in this disclosure, it should be understood that such terminator can also be accompanied by a suitable counterion that balances the positive charge. Exemplary negatively charged counterions include, without limitation, carbonate, bicarbonate, acetate, chloride, bromide, and phosphate, for example. Also, although particular resonance structures can be shown herein, such structures are intended to include all other possible resonance structures.

The present teachings are directed to compositions, sequencing methods, such as Sanger dideoxy sequencing methods, and sequencing kits, that utilize a cationically charged nucleic acid terminator in combination with a discriminatory polymerase. The use of the cationically charged nucleic acid terminator allows for the use of a discriminatory polymerase at a low level as the cationically charged nucleic acid terminator allows for the substantially equivalent incorporation of deoxynucleotides and dideoxynucletides during sequencing. Because such a low amount of the cationically charged nucleic acid terminators are required for the sequencing processes of the present teachings, dye terminator artifacts are substantially reduced or eliminated. In various embodiments, the present teachings are utilized in automated sequencing methods that rely on uniform, size-dependent electrophoretic mobilities to determine whether low peak signals should be included or discarded, and whether overlapping peaks represent fragments of the same length.

As noted above, the sequencing methods and sequencing kits of the present teachings utilize a cationically charged nucleic acid terminator. The cationically charged nucleic acid terminator is shown in structure (I):

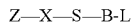

Z—X—S—B-L  (I)

wherein:
Z is a mono-, di-, or tri-phosphate or thiophosphate, or corresponding boranophosphate;
X is O, $CH_2$, S, or NH;
S is a sugar or sugar analogue;
B is a naturally occurring or a synthetic base or nucleobase; and
L is a linker that is alkyl, alkenyl, or alkynyl. Any or all of L, B, S, X, and/or Z are substituted with a moiety which imparts a positive charge to structure (I), and any or all of L, B, S, X, and/or Z are substituted with a reporter moiety.
Generally, the positive charge imparted to structure (I) is stable at conventional physiological or nucleic acid sequencing conditions known in the art.

The base, B, can be any naturally occurring or synthetic base such as Adenine, Thymine, Guanine, or Cytosine, or analogs thereof, such as 7-deazapurine, inosine, universal bases, etc. Suitable analogs include those disclosed in WO 99/06422 and WO 97/28177, both of which are hereby incorporated by reference. The base can also be any suitable nucleobase.

The sugar, S, can be furanose, hexose, mone-di-triphosphates, morpholine, didehydro, dideoxyribose, deoxyribose, dioxalone, oxathialane, analogs thereof, and other suitable sugars utilized in the art.

The linker, L, which can be a moiety that links a reporter moiety to the cationically charged nucleic acid terminator, can be alkyl, alkenyl, or alkynyl and can contain 1 to about 1000 atoms or more and can contain atoms such as C, H, N, O, S and halogens. In general, the linker contains from about 2 to about 500 atoms, from about 2 to about 250 atoms, and even from about 11 to about 25 atoms.

As noted herein, any or all of L, B, S, X and/or Z are substituted with a reporter moiety to allow for detection of products in a sequencing method. The reporter moiety can be, for example, a radioisotope, an electrochemical label, a fluorescent label (i.e., xanthenes, rhodamines, fluoresceins, cyanines, phthalocyanines, squaraines, and Bodipy® dyes), an energy transfer label, a mass spectrometry label, a Raman label, a hapten, a chemilluminescent label, an enzyme, a chromophore, or a combination thereof. The reporter moiety can also be a charged moiety such as Cy5.5, bis-sulfonated carboxyfluorescein, or a dye attached to a charged moiety, such as a carboxyfluorescein attached to cysteic acid or a similar charged species.

The cationically charged nucleic acid terminators disclosed herein are suitable for use in sequencing methods at very low levels due to their unique ability to be incorporated by the discriminatory polymerase. Suitable incorporation of the cationically charged nucleic acid terminators can be obtained using the cationically charged nucleic acid terminators in an amount of less than about 100 pm, and generally less than 50 pm in a 10 µL volume. In some embodiments, the cationically charged nucleic acid terminators can be used in an amount of less than 25 pm in a 10 µL volume, less than 10 pm in a 10 µL volume, less than 5 pm in a 10 µL volume, and even less than 2 pm in a 10 µL volume or 1 pm in a 10 µL volume.

The cationically charged nucleic acid terminator is substituted with at least one cationic moiety that imparts a positive charge to structure (I). This positively charged structure is generally stable at conventional physiological or nucleic acid sequencing conditions. The number of cationic moieties introduced into/onto the cationically charged nucleic acid terminator is not limited, and can be, for example, 1, 2, 3, 4, 5, 6, 7, 8, 9, 10, or even more cationic moieties, depending upon the desired cationic charge for the cationically charged nucleic acid terminator.

The cationic moiety for imparting a positive charge to the nucleic acid terminator can be any suitable cationic moiety which alters the electrophoretic mobility of structure (I). Examples of suitable cationic moieties include amines, higher alkyl amines, aryl amines, imidazoles, and combinations thereof. Additional examples of suitable cationic moieties include tetraalkyl ammonium moieties, trialkyl ammonium moieties, imidazolium moieties, aryl ammonium moieties, iminium moieties, amidinium moieties, guanadinium moieties, thiazolium moieties, pyrazolylium moieties, pyrazinium moieties, pyridinium moieties, and phosphonium moieties.

The cationic moiety and the reporter moiety can be present in the cationically charged nucleic acid terminator in any number of positions. Referring now to FIG. 1, which is illustrative of several representative embodiments of the present teachings but should not be viewed in any manner as limiting the positions of the cationic moiety and the reporter moiety, the cationic moiety or moieties that imparts a cationic charge to the cationically charged nucleic acid terminator and alters the electrophoretic mobility of structure (I) can be attached to the cationically charged nucleic acid terminator in any number of positions including, for example: (1) attached only to Z as shown in FIG. 1(A); (2) attached between Z and X as shown in FIG. 1(B); (3) attached between X and S as shown in FIG. 1(C); (4) attached between S and B as shown in FIG. 1(D); (5) attached between B and L as shown in FIG. 1(E); (6) attached only to L as shown in FIG. 1(F); (7) attached between L and a Reporter moiety as shown in FIG. 1(G); (8) attached only to a Reporter moiety as shown in FIG. 1(H); (9) attached in two positions spaced apart from each other and between any of the positions described herein and shown as one example in FIG. 1(I); and (10) attached between Z and X with a Reporter moiety attached to L as one example in FIG. 1(J). The number of cationic moieties, n, can be from 1 to 1000. One skilled in the art will recognize that in the examples wherein a Reporter moiety is not shown in any of FIG. 1 (A-J), that the Reporter moiety can be attached in any position.

As noted above, the cationically charged nucleic acid terminator can contain multiple linkers and cationic moieties which are alternatively spaced together or apart. Although it is within the scope of the present teachings to attach the cationic moiety to the base only, it is generally believed that the presence of the cationically charged moiety can impact the reactivity of the cationically charged nucleic acid terminator. The cationic moiety can also be made of a number of charged units that are covalently linked together.

The cationically charged nucleic acid terminators disclosed herein and suitable for use in the methods and kits also disclosed herein can be synthesized by any suitable synthetic method. One exemplary non-limiting approach to synthesizing a cationically charged nucleic acid terminator is shown in the Examples below. Additionally, suitable cationically charged nucleic acid terminators can be synthesized utilizing the methods set forth in WO 01/19841 published on Mar. 22, 2001 and hereby incorporated by reference.

As noted above, the cationically charged nucleic acid terminators can be utilized in a sequencing method in combination with a discriminatory polymerase. In some embodiments, such as in a conventional Sanger dideoxy sequencing method, the discriminatory polymerase incorporates deoxynucleotides at a rate that is at least 100 times faster than that of dideoxynucleotides. In some embodiments, such as in a conventional Sanger dideoxy sequencing method, the discriminatory polymerase incorporates deoxynucleotides at a rate that is at least 1000 times faster than that of dideoxynucleotides.

Aspects of the present teachings can be further understood in light of the following examples, which should not be construed as limiting the scope of the present teachings in any way.

EXAMPLES

Examples 1-24 disclose the sequential synthesis of a cationically charged nucleic acid terminator in accordance with the present teachings and suitable for use in the methods and kits disclosed herein. References to compounds found in bold (i.e., A1, A2, A3, etc.) refer to the chemical schemes found in FIGS. 2-9. Unless indicated otherwise, all reagents and anhydrous solvents were purchased from Aldrich Chemicals. Thin layer chromatography (TLC) analysis was conducted on aluminum plates precoated with 250 μm layers of silica gel 60-F254. Compounds were located by UV-VIS lamp and/or by charring with aqueous $KMnO_4$ or ninhydrin/butanol solution. Flash column chromatography purification was carried out using EM Science silica gel 60 angstrom (230-400 Mesh ASTM). NMR spectra were recorded in deuterated solvents ($CDCl_3$, $CH_3OD$, DMSO-d6 and $D_2O$ with an internal $Me_4Si$ standard, δ 0). $^1H$ NMR spectra were recorded at 400 MHz.

Example 1

N-2-Tert-Butoxycarbonylaminoethyl Imidazole

To a stirring solution of 5% (aq) sodium carbonate (25 g, 238 mmol) was added 22.8 g (100 mmol) N-2-aminoethyl imidazole A1 (prepared in accordance with Alvarez-Builla et al., *Synthetic Communications* 21(4):535-544, 1991), followed by 175 mL THF (tetrahydrofuran) and a first portion of di-tert-butyl dicarbonate A2 (25.6 g, 117 mmol). The mixture was stirred at room temperature for 3 h, during which it warmed, cooled, became clear, then cloudy. A second portion of A2 (6 g) was then added and stirred over night at room temperature. The mixture was then diluted to 1000 mL with ethyl acetate (EA). After the solvent layers separated, the aqueous layer was extracted twice with 200 mL of ethyl acetate, and finally with 150 mL of ethyl acetate. The combined organic portions were washed twice with 150 mL portions of brine, dried over $Na_2SO_4$, filtered, and evaporated under reduced pressure to yield 15 g (71 mmole) of A3 as an oil.

Example 2

$N^1$-3-Bromopropyl-$N^3$-2-Tert-Butoxycarbonylaminoethyl Imidazolium Bromide 4.22 g (20 mmol) of N-2-tert-butoxycarbonylaminoethyl imidazole A3 and 20 mL (40 g, 200 mmol) 1,3-dibromopropane A4 were dissolved in 20 mL DMF (dimethylformamide) in a 100 mL flask and heated overnight at 80° C. using an oil bath. When the reaction was complete based on NMR analysis of an aliquot, the DMF was removed by high vacuum rotoevaporation. The concentrated material was chromatographed on a 130 mm×75 mm bed of silica gel 60 (Merck) packed in 20:1 dichloromethane:methanol (DCM:M) eluted with (1) 600 mL of 20:1 DCM:M, (2) 1 L of 10:1 DCM:M, then (3) 2 L of 5:1 DCM:M, during which fractions of 225 mL were collected. TLC analyses of fractions were performed on silica eluted with 5:1 DCM:M, and product was visualized with iodine and ninhydrin. Product-containing fractions were collected and dried under reduced pressure, yielding 6.8 g (16.5 mmol) A5 as an opaque thick oil.

Example 3 t-Boc-Protected Linker Element Containing Three Imidazolium Moieties 3.3 g (8 mmol) of A5 and 10.7 g (60 mmol) A6 were dissolved in 30 mL DMF in a 100 mL flask and heated at 85° C. using an oil bath. After NMR analysis of an aliquot indicated completion of the reaction (after about 16 h of heating), the reaction mixture was filtered through a coarse frit (which removed symmetrical side-product A7) and solvent was removed under high vacuum. The resultant product was dispersed in 35 mL of DCM, poured into 140 mL of THF, and stirred over night, yielding a gummy precipitate in a clear supernatant. After decantation, the precipitate was re-precipitated in the same manner (35 mL DCM/140 mL THF) twice more, yielding 4.14 g (7 mmol) product A8 as a yellow solid in a ratio of about 20:1 relative to starting material A6 based on NMR analysis.

Example 4 t-Boc-Protected Bromide Linker Element Containing Three Imidazolium Moieties t-Boc-protected tri-imidazolium A8 (960 mg, 1.63 mmol) was dissolved in 10 mL warm DMF. A salt precipitate was removed using a 20 mL disposable polypropylene syringe with PTF6 syringe filter. 1,3-Dibromopropane A4 (6.7 g, 33 mmol) was then added and the mixture was heated at 80° C. over night, followed by high vacuum removal of solvent. The product was resuspended in 20 mL DMF, filtered through a medium frit, followed by washing the frit with 3 mL of DMF. The collected solution was subjected to reduced pressure to remove solvent, yielding 1 g of white solid. The white solid was suspended and sonicated in acetonitrile. Solid product was recovered by suction filtration on a medium frit and vacuum dried, yielding 700 mg (0.88 mmol) of A9 white solid.

Example 5

$N^1$-3-Iodopropyl-$N^3$-2-Tert-Butoxycarbonylaminoethyl Imidazolium Iodide

This example describes a reaction similar to that of Example 2, except that 1,3-diiodopropane was used in place of 1,3-dibromopropane.

A3 (2.2 g, 10 mmol, see Example 1 for synthesis) and 1,3-diiodopropane A10 (11 g, 37.3 mmol) were dissolved in 25 mL THF in a 50 ml flask equipped with a reflux condenser, and the mixture was refluxed in an oil bath at 65° C. over night, forming a large precipitate. After refluxing, the flask was removed from the oil bath and allowed to cool to room temperature. The solid was removed by filtration on a medium frit, chased with 5 mL THF, and then dried under high vacuum, yielding 1.2 g of solid that was identified as the adduct of 1,3-diiodopropane A10 with two molecules of A3. (This adduct, A11, was not used further in this example.) The THF filtrate was chromatographed on a 50 by 50 mm column of silica with 5:1 DCM/M. Product-containing fractions were combined, rotoevaporated and then rechromatographed on a 50 by 50 mm silica column as above with 10:1 DCM:M and then 5:1 DCM:M. Except for an early fraction that contained a substantial amount of residual A10, product-containing fractions were pooled and evaporated, yielding 2.8 g (5.5 mmol) of gummy oil that solidified into a soft yellow solid.

Example 6

$N^1$-3-Bromopropyl-$N^3$-3-Carboxypropyl Imidazole Ethyl Ester 4.4 g (24.2 mmol) of N-3-carboxypropyl imidazole ethyl ester B1 and 13 mL (24.4 g, 121 mmol) 1,3-dibromopropane (A4) were dissolved in 25 mL DMF in a 100 mL flask and heated over night at 80° C. The DMF was removed under reduced pressure, yielding 10 g of a yellow oil. The oil was chromatographed on a 75 mm by 150 mm bed of silica gel 60 packed in 20:1 DCM:M, that was eluted with (1) 1 L of 20:1 DCM:M, (2) 1 L 10:1 DCM:M, then (3) 3 L of 4:1 DCM:M (225 mL fractions). Thin layer chromatography (TLC) analyses of fractions were performed on silica eluted with 5:1 DCM:M, and product was visualized with iodine. Product-containing fractions were collected and concentrated under reduced pressure, yielding 7.6 g (19.8 mmol) B2 as an opaque oil.

Example 7

Ethyl Ester of Linker Element Containing Three Imidazolium Moieties

Compounds B2 (3.6 g) and A6 (14 g, prepared in accordance with Díez-Barra, E., et. al., *Heterocycles* 34(7):1365-1373, 1992) were dissolved in DMF (15 mL) in a 250 mL flask, and the reaction was heated at 80° C. over night. Solvent was then removed under reduced pressure, and the resultant product was dispersed in 40 mL DCM followed by addition of 120 mL of THF. After the mixture was stirred at room temperature for one hour, product was collected by suction filtration on #50 Whatman filter paper. The resultant pasty solid, which melts very quickly in ambient air, was transferred to a 250 mL Erlenmeyer flask and dispersed again in 40 mL of DCM, followed by addition of 120 mL THF. After the mixture was stirred for 1 h, product was collected on #50 Whatman filter paper, transferred to a flask, and subjected to high vacuum, yielding 4.5 g of solid. NMR analysis indicated a ratio of product compound B4 to compound A6 of about 33:1 (based on integrating the imidazole protons at 7.7 ppm), and a ratio of desired product B4 to symmetrical diester B3 of about 14 (based on integrating the imidazolium protons at 9.4, 9.5 and 9.6).

Example 8

Linker Element Containing Six Imidazolium Moieties 680 mg of A9 (860 µmol, Example 4) was dissolved in 8 mL DMF by heating in an 80° C. oil bath. 500 mg (890 µmol) of solid B4 was added, which dissolved slowly with heating in the oil bath followed by formation of a precipitate. After a total of about 15 h of heating in the oil bath, the resultant solid was collected slowly on a 45 mm diameter #50 Whatman filter and then subjected to high vacuum over night, yielding 830 mg of doubly protected C1.

Product C1 was dissolved in 5 mL conc HCl (12 M) and refluxed for 1 h. The mixture started bubbling as soon as the HCl was added. Solvent was then removed under reduced pressure, yielding a thick oil. Ten mL water was added and then removed under reduced pressure, yielding a thick paste. High vacuum over night yielded 850 mg (850 µmol) of solid C2. NMR analysis in $D_2O$ (with slight amount of $K_2CO_3$ to aid dissolution) indicated that the t-butyl group and ethyl ester had been hydrolyzed.

Example 9

N-trimethylsilylimidazole D1 (2.8 g, 20 mmol) and ethyl 4-bromobutanoate D2 (4 g, 20 mmol) were dissolved in DMF (8 mL) in a 25 mL flask and heated over night in a 70° C. oil bath. The reaction was poured into 100 mL of water and was saturated with solid sodium bicarbonate. The resulting liquid was decanted into a separatory funnel, chased with 10 mL of water, and extracted three times with 100 mL portions of DCM. Analysis of each DCM extract by thin layer chromatography (silica, 5:1 DCM/M visualized with iodine) indicated that all product was extracted by the second extract. The first and second DCM extracts were pooled, washed with water and then by brine, dried with $Na_2SO_4$, filtered, and evaporated to form an oil. The oil was chromatographed on silica (50 by 180 mm, 20:1 DCM/M). Product fractions were pooled and rotoevaporated followed by high vacuum to remove residual solvent, yielding 1.3 g (7.1 mmol) of D3 as a light yellow oil.

Example 10

D3 (1.82 g, 10 mmol) and A4 (10 g, 50 mmol) were mixed in DMF (10 mL) in a 50 mL flask and heated at 70° C. for 16 h. The DMF was removed by rotoevaporation under high vacuum. The product was chromatographed on silica (50 by 150 mm with 10:1 DCM/M). Product-containing fractions were analyzed by TLC (silica developed with 5:1 DCM:M), visualized with iodine, pooled and rotoevaporated, yielding 2.88 g (7.5 mmol) D4 of a cloudy oil.

Example 11

In a 250 mL 3-neck flask with mechanical stirring and reflux condenser with argon atmosphere and bubbler, imidazole E1 (27.25 g, 400 mmol), $(CH_3(CH_2)_3)_4N)HSO_4$ (3.86 g, 11.4 mmol), and KOH (26.8 g, 480 mmol) were added with stirring, forming a thick liquid. After 45 min, 1,2-dichloroethane E2 (19.8 g, 15.2 mL, 200 mmol, 1 equiv) was added in one portion and heated gently with a heating mantle, during which gas was evolved and the mixture became warm. The heating mantle was then removed and the reaction was stirred overnight. The reaction was then diluted with 100 mL of ethanol and filtered on #2 filter paper on a Buchner funnel. The solid was washed with 20 mL ethanol. The solid was dried under reduced pressure, dissolved in about 200 ml of 8:1 DCM/M, and chromatographed on a silica column, 75 by 180 mm, packed with 10:1 DCM/M. Elution was performed with 10:1 DCM/M. Fractions were analyzed by TLC with 5:1 DCM/M and visualized using iodine. Fractions that contained 1,2-diimidazole E3 were combined, dried, and rechromatographed through a 75 by 180 mm silica column packed with 10:1 DCM/M. Elution was performed initially with 10:1 DCM/M until TLC analysis of fractions showed that imidazole E1 stopped eluting, then with 5:1 DCM/M until E3

Example 12

D4 (2.88 g, 7.52 mmol) and E3 (609 mg, 3.76 mmol, 1 equiv) and 10 mL DMF were placed in a 50 mL flask and heated at 70° C. for 16 h, forming a white solid. The solid was mixed with about 25 mL acetonitrile and sonicated until lumps were broken up. The solid was then collected by suction filtration on a medium frit and washed with additional acetonitrile, with a final volume of about 40-50 mL of acetonitrile washings. This helped remove triimidazole monoester E4, which was not used further in these experiments. The collected solid was transferred to a flask and subject to high vacuum over night, yielding 2.25 g (2.4 mmol) of white solid E5.

Example 13

N-2-aminoethyl imidazole hydrobromide A1 (2.29 g, 10 mmol) was suspended in ethanol (30 mL), followed by addition of triethylamine (TEA, approx. 3 mL). The reaction mixture initially became clear and then formed a precipitate. To this mixture was added $CF_3CO_2Et$ (F1, approx. 2 mL), and the mixture was stirred at room temperature over night. The precipitate was removed by filtration, and the filtrate was dried by rotoevaporation and high vacuum. The solid residue was suspended in 30 mL THF. Undissolved solid was removed by filtration, and the filtrate was dried by rotoevaporation and high vacuum. The resulting solid was heated in 25-30 mL toluene until it melted, followed by removal of the toluene by rotoevaporation. Addition of toluene was repeated, followed by removal of toluene under high vacuum, yielding 2.0 g (9.6 mmol) F2 in a ratio of about 8:1 relative to residual TEA based on NMR analysis.

Example 14

F2 (4.17 g, 20 mmol) was dissolved in about 10 mL THF, and an opalescent precipitate was removed by filtration and chased with 10 mL THF, after which bromoacetate phenyl ester F3 (5.16 g, 24 mmol) was added. The mixture was heated to reflux with a heat gun twice, and was then allowed to stand overnight at room temperature, forming crystals. To this mixture was added 10 mL ether, and the crystals were suspended by sonication, followed by suction filtration and washing with a little THF. The filtered solid was dried under vacuum, yielding 6.85 grams (16.2 mmol) of product F4.

Example 15

F4 (2.11 g, 5 mmol) was dissolved in acetonitrile (10 mL), producing a hazy solution. To this was added solid N-2-aminoethyl imidazole A1 (600 mg, 5.4 mmol) with stirring at room temperature, followed by brief gentle warming, then stirring at room temperature for about 2 h, resulting in formation of adduct F5. Solvent was removed by rotoevaporation at 40° C., and 10 mL of acetonitrile was added, followed by bromoacetate phenyl ester F3 (1.11 g, 5.16 mmol) in one portion with stirring at room temperature. The mixture was then warmed gently by heat gun over about 30 min, then rotoevaporated at 40° C. to form a glass. The glassy material was triturated with 45 mL of THF over night. Solid product was collected by filtration on a medium frit, yielding 2.8 g. This was triturated with 30 mL acetonitrile, warmed gently, then stirred in an ice bath, then warmed to room temperature over 2 h. Solid product was collected by filtration, yielding 1.4 g (2.1 mmol) of F6.

Example 16

F4 (1.46 g, 3.5 mmol) was dissolved in about 12 mL of acetonitrile (ACN) with sonication and then was added to a stirred solution of F7 (990 mg, 5.46 mmol) in ACN (2 mL) and stirred at room temperature for about 2 h. Most of the acetonitrile was removed by rotoevaporation (leaving a volume of about 2 mL), and 50 mL ether was added and mixed. The opaque ether layer was decanted, and 20 mL of ether was added, mixed, and then decanted. The acetonitrile layer was dried under high vacuum, producing a sticky foam. The sample was dissolved in aq HBr (10 drops HBr/L of water), applied to a C18 reverse phase silica column (40 by 60 mm, BakerBond Octadecyl 40 Micron Prep LC packing material, PN 7025-01 from J. T. Baker Inc., USA) packed with aq HBr, and eluted with 400 mL of aq HBr, then 220 mL of 200:20 aq HBr/ACN, then 230 mL of 200:30 aq HBr/ACN, then 240 mL of 200:40 aq HBr/ACN. Fractions were analyzed by silica TLC plates and visualized with ninhydrin and/or molybdic acid stain solution (12 g $(NH_4)_8Mo_7O_{24}.4H_2O$, 0.5 g cerric ammonium nitrate, 50 mL $H_2SO_4$, and 450 mL water). Product fractions were combined and evaporated under high vacuum to produce F8 as a sticky foam (1.14 g, 2.24 mmol).

Example 17

F8 was dissolved in 15 mL water and 5 mL acetonitrile, 5 mL concentrated $NH_4OH$ was then added. After 3 h, solvent was removed by rotoevaporation, the solid residue was dissolved in aq HBr as above and chromatographed on the same column as above (which had been washed with methanol and reequilibrated in aq HBr). Elution was performed using aq HBr, then 100:5 aq HBr/ACN, then 100:10 aq HBr/ACN. Fractions were spotted on silica TLC plates and visualized with ninhydrin. Ninhydrin-reactive fractions were pooled and evaporated. The product was suspended in acetonitrile, and crystals were broken up by sonication. White solid was collected by vacuum filtration on a medium frit and vacuum-dried, yielding 740 mg (1.5 mmol) white solid F9.

Example 18A

F9 (11 mg, 22 μmol) was dissolved in 300-500 μL methanol (MeOH) with one drop triethylamine (TEA), and rhodamine dye NHS ester F10 (11 mg, 16 μmol, see Lee et al., *Nucl. Acids Res.* 25:2816-2822, 1997) was added as a solid. After 1 h, the mixture was diluted with 0.1% trifluoroacetic acid (TFA) in water and loaded on a reverse phase C18 silica column (10 by 40 mm, from J. T. Baker, supra) that was then eluted with 100:10, 100:20, 100:30, 100:35 0.1% TFA:acetonitrile (110-135 mL each). The colored eluent was collected in 25 mL fractions, each fraction was concentrated and analyzed by HPLC. Fractions 3-7 were pooled and evaporated. Half of the material was submitted for mass spectrometric analysis, and the other half was saved to be used as an HPLC standard. The MS spectrum (MW=814.73) was consistent with structure F11.

Example 18B

As an alternative to the procedure in Example 18A, F9 (7.4 mg, 15 μmol) was dissolved in a mixture of 140 mg formamide and 5.3 mg TEA. To this was added F10 (8.5 mg, 14.3

µmol) with stirring. HPLC analysis indicated that coupling was complete within about 2 h, forming F11.

Example 18C

As a second alternative to the procedure in Example 18A, F9 (7.6 mg, 15.4 µmol) was dissolved in 5% aq NaHCO$_3$ solution (95 mg) and THF (2 drops) was layered on top. F10 (8.5 mg, 14.3 µmol) was added as a solid in one portion and the mixture was sonicated. HPLC analysis of aliquots (0, 3 h, 5.5 h, and 19 h after sonication) showed a steady increase in the product peak for F11 and a steady decrease in the NHS ester F10. The reaction was desalted on a small reverse phase column by loading the sample in 0.1% TFA (aq), washing with 10 column volumes of 0.1% TFA, and eluting with 4:1 acetonitrile:0.1% TFA. After evaporation of solvent, mass spectrometric analysis confirmed that the large peak is product F11 (MW 814.73).

Example 19

G1 (4-aminomethyl benzoic acid, 7.5 g, 50 mmol) was suspended in 75 mL DCM, and 10 mL TEA was added, followed by 20 mL trifluoroacetic anhydride (TFAA), and then 10 mL more TEA, so that all reactants dissolved after a while. The mixture was diluted with 500 mL ethyl acetate (EA), washed two times with 1 N HCl (100 mL portions), then two times with 100 mL portions of brine. The organic layer was dried over Na$_2$SO$_4$, filtered, rotoevaporated, and subjected to high vacuum to remove some of the excess trifluoroacetic acid (TFA). The dried material was redissolved in 300 mL 5% NaHCO$_3$ solution and washed two times with EA (100 mL portions), acidified with 6 N HCl, and extracted two times with EA (250 mL portions). The combined EA layers were washed two times with brine (100 mL portions), then dried over Na$_2$SO$_4$, filtered, and rotoevaporated. The collected product was then crystallized from 100 mL EA, yielding 6.0 g of crystalline 4-(trifluoroacetyl)aminomethyl benzoic acid (first crop) and an additional 1.8 g in a second crop (total 7.8 g).

2.45 g of the 4-(trifluoroacetyl)aminomethyl benzoic acid and 1.4 g of N-hydroxysuccinimide (NHS) were dissolved in 25 mL of THF. To this was added 22 mL of a 0.5 M solution of dicyclohexyl carbodiimide (DCC) in DCM and the mixture was stirred at room temperature. After 45 minutes, precipitated dicyclohexylisourea (DCU) was filtered from the solution, and the solution was diluted with EA to 200 mL final volume. This was washed with two 50 mL portions of 1 N HCl, then with two portions of brine, followed by drying with Na$_2$SO$_4$. The dried solution was filtered, rotoevaporated, and the dried product was crystallized from ethanol, yielding 2.8 g (8.1 mmol) p-(N-trifluoroacetyl-aminoethyl)benzoate NHS ester G2 as a white solid. Silica TLC eluted with ethyl acetate showed one spot.

Example 20

4'-aminomethyl fluorescein compound G3 (220 mg, 0.5 mmol) (see Shipchandler et al., *Anal. Biochem.* 162:89-101 (1987), U.S. Pat. No. 4,510,251, and Lee et al., *Nucl. Acids Res.* 25:2816-2822 (1997)) was dissolved in 5% Na$_2$CO$_3$, forming a dark orange solution, to which was then added about 3 mL THF. To this mixture was added G2 (200 mg, 0.58 mmol) as a solid. After stirring for 1 h at room temperature, an aliquot (100 µL) was removed and partitioned between ethyl acetate (EA) and 5% HCl (1 mL each). TLC analysis on silica in 5:1 DCM:MeOH indicated that some residual starting material G3 remained at baseline, so another 50 mg (0.14 mmol) of G2 was added to the main reaction mixture and stirred for 30 min more, followed by addition of 5% aqueous HCl to a final volume of 50 mL. This mixture was then extracted with 30 mL EA, then 20 mL EA, and the combined EA layers were washed with two portions of brine and dried over night over Na$_2$SO$_4$. The dried EA solution was filtered and then rotoevaporated. The residue was chromatographed on a silica column (25 by 80 mm) eluted with 10:1 DCM/ MeOH containing 1% acetic acid (AA). Product-containing fractions were combined and rotoevaporated and partitioned between EA (100 mL) and 1 N HCl (25 mL), washed with brine (25 mL), and dried over Na$_2$SO$_4$. The EA layer was rotoevaporated and rechromatographed on silica (25 by 80 mm) with 15:1 DCM:M containing 1% AA. All product fractions were combined and rotoevaporated, then resuspended and coevaporated from THF/toluene (5 mL/30 mL) twice, then subject to high vacuum, yielding 300 mg (0.47 mmol) of product G4.

Example 21

Product G4 was dissolved in 6 mL of THF, and 110 mg (1 mmol) of N-hydroxysuccinimide (NHS) was added. The reaction mixture was sonicated, followed by filtration though a plug of glass wool. To the filtered reaction mixture was added 1.4 mL of a 0.5 M DCC/DCM solution (0.7 mmol dicyclohexyl carbodiimide in dichloromethane). After about 35 min, TLC showed very little starting material, so the reaction mixture was filtered through a frit chased with EA, then diluted to about 75 mL with about 25 mL EA, washed with 0.5 N HCl, then twice with brine, and dried over Na$_2$SO$_4$. The dried solution was filtered, rotoevaporated, reconstituted in EA, sonicated, followed by removal of precipitated DCU by filtration and rotoevaporation of the filtered reaction mixture. The reaction mixture was then chromatographed on a silica column (25 by 80 mm) using 20:1 DCM/MeOH. Fractions were analyzed by TLC, and product-containing fractions were pooled and rotoevaporated, yielding 350 mg (0.47 mmol) product G5.

Example 22

Poly-imidazole hexamer C2 (650 mg, 516 µmol, prepared supra) was dissolved in about 4 mL of formamide, then G5 (220 mg, 300 µmol), dissolved in about 5 mL of formamide, was added. The flask containing G5 was washed (chased) two times with one mL portions of formamide into the mixture of C2 and G5, then several drops of TEA were added until the reaction started to become orange. The reactions was allowed to stand at room temp for 2 h and then was analyzed by HPLC (4.6×150 mm C18 column, gradient of 5% to 95% B at 1 mL/min over 20 minutes, A=0.1% aqueous TFA, B=0.1% TFA in acetonitrile). The largest peak at 9.66 was the product. The reaction mixture was then diluted to about 200 mL with 0.1% aqueous TFA and loaded on a reverse phase silica column (20×60 mm) and eluted with 100:15 0.1% TFA:acetonitrile, then 100:25, then 100:30, then 100:35 (~200 mL each). Product-containing fractions were analyzed by HPLC and the best were pooled, diluted with 2 volumes of 0.1% aq TFA, and trapped on a 10 by 10 mm pad of reverse phase silica, washed with a small volume of 0.1% aq TFA, then eluted with methanol containing about 1 to 2% water. Rotoevaporation and drying under high vacuum yielded 300 mg (147 µmol) of yellow glassy residue G6. This product was dissolved in methanol and split into two 50 mg batches and one 200 mg batch that were also evaporated and placed under high vacuum. HPLC showed a single product peak, and three distinct amide NH hydrogen peaks were observed, consistent with the expected product.

Example 23

Activated Energy Transfer Dye Conjugate Containing Six Imidazolium Moieties 48 mg (23 μmol) of G6 was dissolved in 3-4 mL MeOH and treated with 1 mL of 10% NaOH for about 2 h. The solution was then diluted with 0.1% aq trifluoroacetic acid (TFA) to 75 mL, followed by dropwise addition of neat TFA until the pH was about 2. The solution was then passed through a 15 mm by 15 mm plug of reverse phase silica gel (BakerBond Octadecyl 40 Micron Prep LC packing material, PN 7025-01 from J. T. Baker Inc., USA) to trap colored components, then eluted with 100:1 MeOH/$H_2O$ containing about 0.3% TFA. The flow of the column was stopped for 10 to 15 min between the collection of each fraction. Removal of solvent from product-containing fractions yielded about 50 mg of deprotected product G7 (having removed the trifluoroacetyl protecting group). This was dissolved in MeOH.

About 80% of G7 solution was stripped and then subjected to high vacuum, yielding 42 mg of G7. This was dissolved in 1 mL of DMF, and 15.5 mg of rhodamine dye NHS ester F10 (supra) was added, followed by about 100 μL of TEA. HPLC of an aliquot after about 25 min indicated that very little starting material remained, and that a large product peak had appeared. After about 2 h, the solution was diluted with aqueous TFA to about 75 mL loaded on a 60 mm by 15 mm reverse phase silica column (J. T. Baker, supra), and eluted with 20:100 (240 mL), 30:100 (260 mL), and 40:100 (280 mL) acetonitrile/aq 0.3% TFA. Product-containing fractions (50 mL each) were identified by HPLC and NMR.

The combined product fractions were diluted 2.5-fold with water and passed through a 10 mm by 15 mm pad of reverse phase C18 silica (J. T. Baker, supra). The trapped compound was washed with 1:10 acetonitrile/aqueous 0.5% TFA and then eluted with 100:1 MeOH/$H_2O$ containing about 0.3% TFA. During elution, the flow was stopped for 15 minutes between fractions. The product fractions were concentrated under reduced pressure and then dissolved in 1 mL DMSO (dimethylsulfoxide) and precipitated with 14 mL of ether in a 15 mL Falcon tube. After 2 more precipitations from DMSO/ether, the sample was precipitated twice with DMSO-$d_6$-ether. After removal of the ether by high vacuum, the sample was dissolved in DMSO-$d_6$ for NMR analysis, confirming that free acid G8 was obtained.

The G8 product in the NMR sample tube was treated with 10 mg of TSTU (O—(N-Succinimidyl)-1,1,3,3-tetramethyluronium tetrafluoroborate) and then with 5 microliters of triethylamine. After 1 hour, NMR analysis indicated that the desired NHS(N-hydroxysuccinimide) ester G9 had formed. The sample was transferred to a 15 mL Falcon tube with the aid of a small amount of DMSO and precipitated with 13 mL of ethyl acetate. After decantation and vacuum concentration, the sample was dissolved in DMSO-$d_6$. NMR analysis showed a singlet at 2.5 ppm integrating as 4 protons, indicating formation of NHS ester G9. The sample was then precipitated with ether in portions in a 1.5 mL Eppendorf tube and vacuum dried.

Example 24

Nucleotide Synthesis

Compound H1 was dissolved in 50 μL of dry dimethylformamide followed by addition of 15 μL triethylamine. Dye-NHS ester G9 (supra) was added as a solution (15 μL of a 1 mg Dye-NHS ester per 12 μL of DMSO) and stirred in the dark overnight at room temperature. The reaction mixture was purified by cation exchange chromatography (CE-HPLC) (Example 25). Product-containing fractions were concentrated. Final product H2 was dried in vacuo and diluted with 250 mM CAPSO buffer, pH 9.6, to a desired concentration.

Example 25

In this Example, the cationically charged nucleic acid terminator (H2) synthesized in Examples 1-24 was utilized in a Sanger dideoxy sequencing method and its incorporation was compared to the incorporation of a commercially available terminator (BigDye® terminator from the BigDye® v3.1 Cycle Sequencing Kit commercially available from Applied Biosystems (Foster City, Calif.) under Part No. 4337454) in an identical Sanger dideoxy sequencing method. Three different polymerases were utilized in the Sanger dideoxy sequencing methods comparing the incorporation of H2 and the BigDye® terminator: (1) AmpliTaq® DNA Polymerase FS; (2) BigDye Polymerase v3.1; and (3) AmpliTaq® DNA Polymerase CS. All three of these polymerases are commercially available from Applied Biosystems (Foster City, Calif.). Polymerases (1) and (2) contain mutations designed to lessen the discrimination of dideoxynucleotides as compared to deoxynucleotides in Sanger dideoxy sequencing, whereas polymerase (3) did not contain such a mutation; that is, polymerase (3) was a discriminatory polymerase.

For the reaction mixtures including the AmpliTaq® DNA Polymerase FS or the BigDye® Polymerases v3.1, the buffer utilized was from a BigDye® v3.1 Cycle Sequencing Kit. For the reaction mixtures including the AmpliTaq® DNA Polymerase CS, the buffer utilized was from an AmpliTaq® DNA Polymerase CS Kit. pGEM template and -21M13 forward sequencing primers (commercially available from Applied Biosystems (Foster City, Calif.)) were used in all reaction mixtures. A premix of reaction components was prepared according to Tables 1, 2, and 3 where all quantities are given on a per reaction basis for 10 μL reaction volume:

TABLE 1

| (AmpliTaq ® DNA Polymerase FS) | |
| --- | --- |
| Buffer (BigDye ® v3.1) | 2.0 μL |
| dATP/dCTP/dUTP/dITP mix of 2 mM of each component | 0.25 μL |
| Template pGEM-3Zf(+)0.2 μg/mL | 1.0 μL |
| Primer-21M13 (forward) 0.8 pmol/μl | 2.0 μL |
| AmpliTaq ® DNA Polymerase FS | 0.125 μL |
| Water | 2.125 μL |
| Total | 7.5 μL |

TABLE 2

| (BigDye ® Polymerase v3.1) | |
| --- | --- |
| Buffer (BigDye ® v3.1) | 2.0 μL |
| dATP/dCTP/dUTP/dITP mix of 2 mM of each component | 0.25 μL |
| Template pGEM-3Zf(+)0.2 μg/mL | 1.0 μL |
| Primer-21M13 (forward) 0.8 pmol/μl | 2.0 μL |
| BigDye ® Polymerase v3.1 | 0.125 μL |
| Water | 2.125 μL |
| Total | 7.5 μL |

TABLE 3

| (AmpliTaq ® DNA Polymerase CS) | |
| --- | --- |
| Buffer (AmpliTaq ® DNA Polymerase CS Buffer) | 1.0 µL |
| dATP/dCTP/dUTP/dITP mix of 2 mM of each component | 0.25 µL |
| Template pGEM-3Zf(+)0.2 µg/mL | 1.0 µL |
| Primer-21M13 (forward) 0.8 pmol/µl | 2.0 µL |
| AmpliTaq ® DNA Polymerase CS | 1.0 unit contained in buffer volume |
| Water | 3.25 µL |
| Total | 7.5 µL |

Final reaction mixtures for evaluation were assembled in individual wells of a MicroAmp® Optical 96-well reaction plate. Final reaction mixtures had a volume of 10 µL, which included 7.5 µL of the premixtures described in Tables 1, 2, and 3. From 1 to 25 pm of charged nucleic acid terminator (H2) was added to each reaction volume along with a sufficient amount of water to bring the total reaction mixture to 10 µL. Reactions were thermocycled in an Applied Biosystems GeneAmp® PCR System 9700 as follows: 96° C. for 1 minute; 35 cycles of 96° C. for 0.1 minutes, 50° C. for 0.05 minutes, and 60° C. for 4 minutes; and finally a 4° C. hold cycle.

All reactions were purified by spin-column purification over Centri-Sep® Spin Columns according to manufacturers instructions (Princeton Seperations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300 times gravity for 2 minutes, removed from the wash tube, and then inserted into a sample collection tube. The reaction mixture was carefully loaded onto the gel material. Columns were centrifuged in a variable speed microcentrifuge at 1300 times gravity for 2 minutes.

Eluted samples were used directly for sequencing on an Applied Biosystems 3100 Genetic Analyzer. Electophoresis on the 3100 Genetic Analyzer was performed with a sieving polymer (POP-7™ polymer) and a capillary adapted for DNA sequencing analysis (50 cm). The sieving polymer included nucleic acid denaturants. Samples were electrokinetically injected onto the capillary and run for 60 minutes at 15 kV with the outside wall of the capillary maintained at 50° C.

Figure 10:
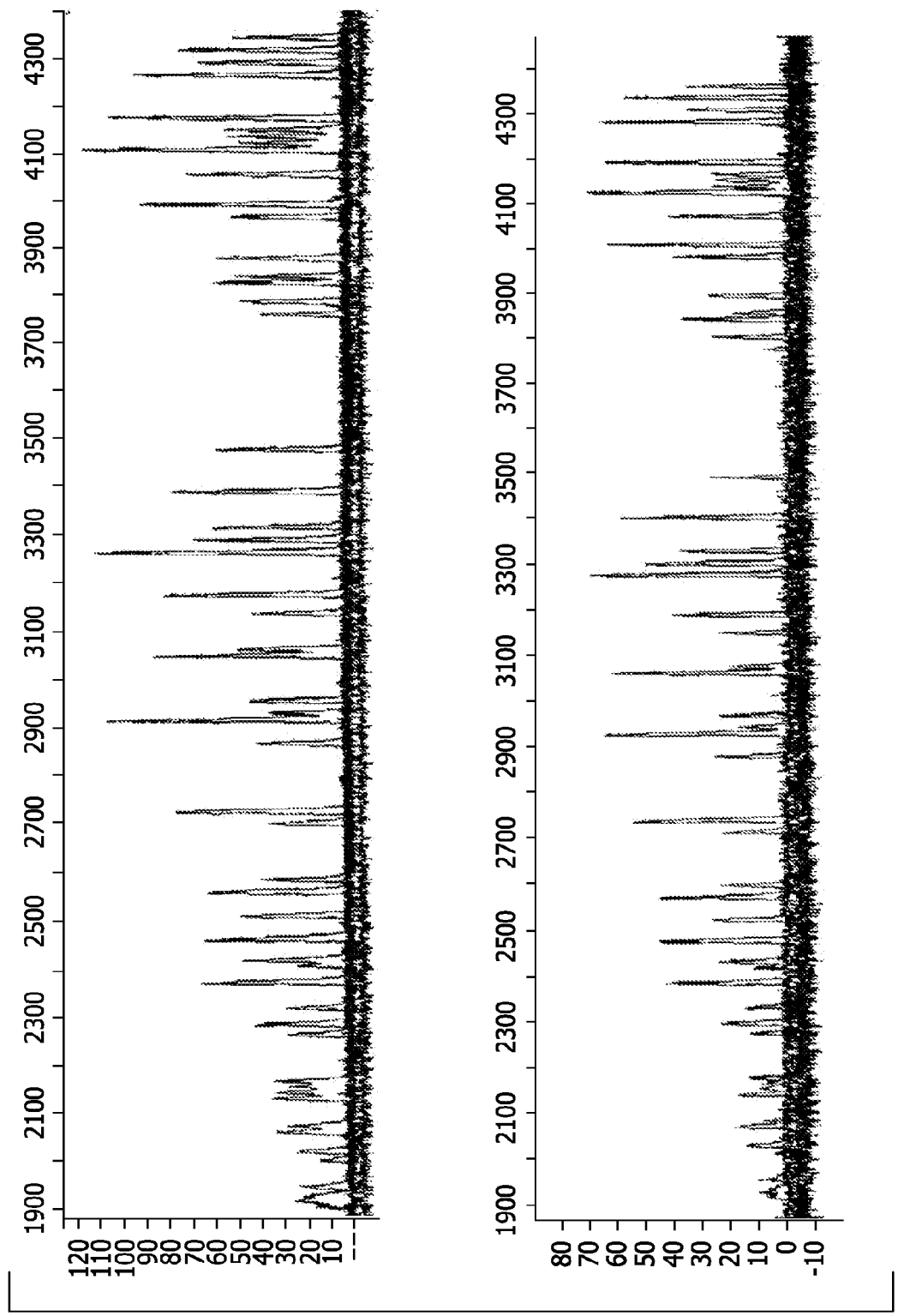
FIGS. 10-11 show electropherograms as referred to in the Examples.
Figure 11:
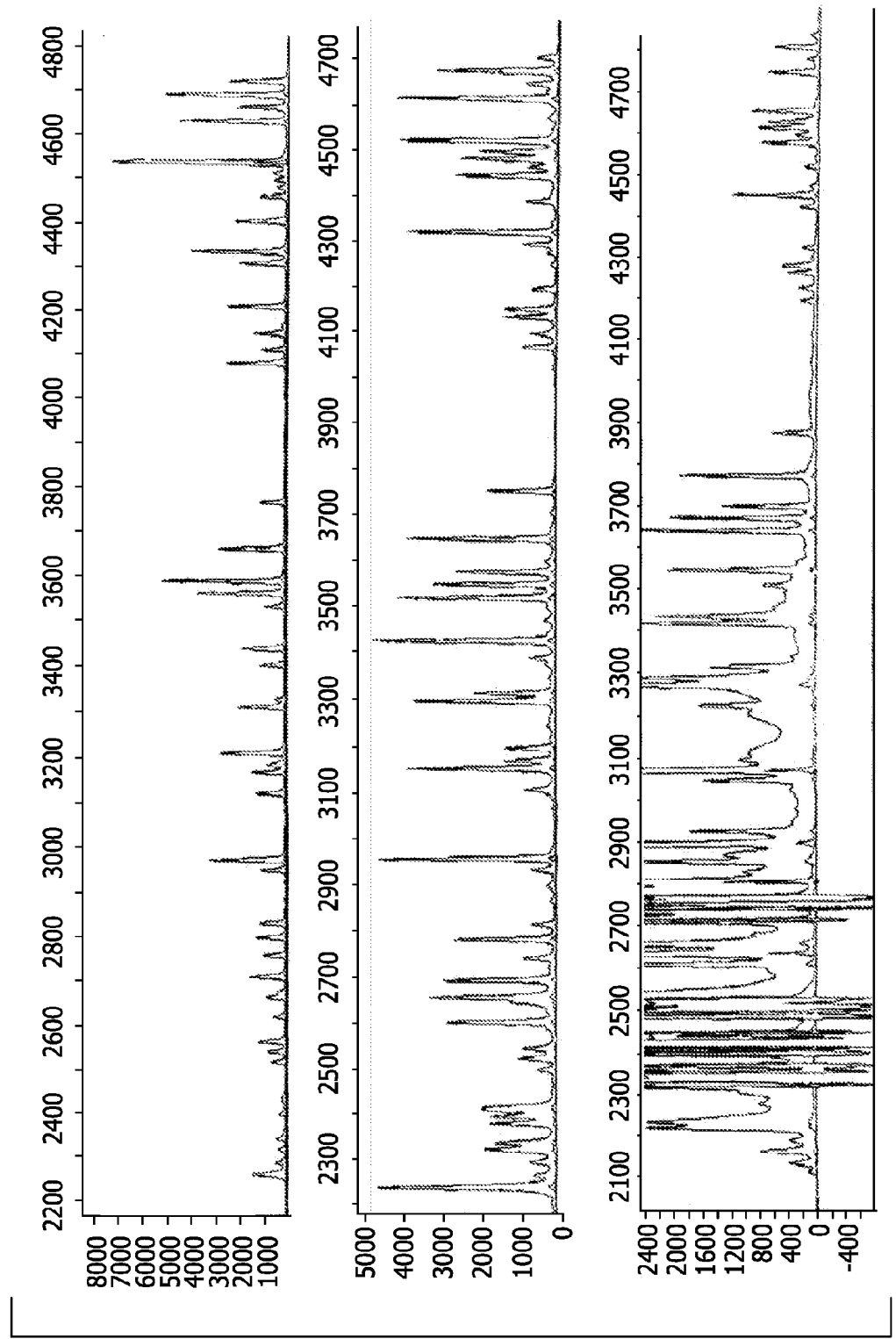

The results of this Example are shown in FIGS. 10 and 11. FIG. 10 shows the results of the reaction using the BigDye® terminator from the BigDye® v3.1 Cycle Sequencing Kit in combination with the AmpliTaq® DNA Polymerase FS (1 pm concentration) and BigDye® Polymerase v3.1 (1 pm concentration). The AmpliTaq® DNA Polymerase CS is not shown in FIG. 10 as even at 250 pm of BigDye® terminator, no incorporation was found. The electropherograms in FIG. 10 are only a representative sample at the beginning of the sequence, and show incorporation of the BigDye® terminator with both polymerases.

FIG. 11 shows the results of the reaction using the charged nucleic acid terminator H2 with all three polymerases tested. With regard to the AmpliTaq® DNA Polymerase FS (1 pm concentration) pattern, the pattern is top heavy, as indicated by the early off-scale peaks. A lower amount of terminator can be used to bring the peaks on scale and more even across the pattern. It is shown that from the later part of the pattern that the relative peak pattern is similar to that of the BigDye® Polymerase v3.1 (2 pm concentration). The AmpliTaq® DNA Polymerase CS (1 pm concentration) pattern shows a higher vertical scale, suggesting excellent incorporation of the H2 terminator by this Polymerase. Additionally, it shows excellent incorporation of the H2 terminator while the Big-Dye® terminator was not incorporated at all with this Polymerase.

What is claimed is:

1. A kit for sequencing a polynucleotide sequence, the kit comprising:
   (a) a cationically charged nucleic acid terminator, the cationically charged nucleic acid terminator comprising a labeled compound of structure (I):

Z—X—S—B-L    (I)

wherein Z is selected from the group consisting of a monophosphate, a di-phosphate, a tri-phosphate, a thiophosphate, and a boranophosphate;
   X is selected from the group consisting of O, $CH_2$, S, and NH;
   S is selected from the group consisting of a sugar and a sugar analogue;
   B is selected from the group consisting of a naturally occurring base, a synthetic base, and a nucleobase;
   L is a linker that is selected from the group consisting of alkyl, alkenyl, and alkynyl;
   wherein L is substituted with a cationic moiety comprising more than one charged units that are covalently linked together which imparts a positive charge to structure (I), and wherein at least one of L, B, S, X, or Z is substituted with a reporter moiety;
   each of the charged units is an imidazolium moiety; and
   (b) a discriminatory polymerase that is exonuclease minus.

2. The kit of claim 1, wherein the discriminatory polymerase is a *Thermus aquaticus* DNA polymerase.

3. The kit of claim 1, wherein the discriminatory polymerase is an *Escherichia coli* DNA polymerase.

4. The kit of claim 1, wherein the discriminatory polymerase is a Pfu DNA polymerase from *Pyrococcus furiosus*.

5. The kit of claim 1, wherein the discriminatory polymerase is a DNA polymerase from *Bacillus stearothermophilus*.

6. The kit of claim 1, wherein L contains up to about 1000 atoms.

7. The kit of claim 1, wherein L contains from about 2 to about 500 atoms.

8. The kit of claim 1, wherein L contains from about 11 to about 250 atoms.

9. The kit of claim 1, wherein L contains from about 18 to about 25 atoms.

10. The kit of claim 1, wherein L further comprises the reporter moiety.

11. The kit of claim 10, wherein the reporter moiety is selected from the group consisting of a radioisotope label, an electrochemical label, a fluorescent label, an energy transfer label, a mass spectrometry label, a Raman label, a hapten, a chemiluminescent group label, an enzyme, a chromophore label, and combinations thereof.

12. The kit of claim 11, wherein the reporter is a fluorescent label or an energy transfer label.

13. A kit for sequencing a polynucleotide sequence, the kit comprising:
   a cationically charged nucleic acid terminator, the cationically charged nucleic acid terminator comprising a labeled compound of structure (I):

Z—X—S—B-L    (I)

wherein Z is selected from the group consisting of a monophosphate, a di-phosphate, a tri-phosphate, a thiophosphate, and a boranophosphate;
X is selected from the group consisting of O, $CH_2$, S, and NH;
S is selected from the group consisting of a sugar and a sugar analogue;
B is selected from the group consisting of a naturally occurring base, a synthetic base, and a nucleobase;
L is a linker that is selected from the group consisting of alkyl, alkenyl, and alkynyl;
wherein L is substituted with a cationic moiety comprising more than one charged units that are covalently linked together which imparts a positive charge to structure (I), and wherein L is substituted with a reporter moiety;
each of the charged units is an imidazolium moiety; and
a polymerase that is exonuclease minus.

* * * * *